United States Patent [19]
Richter

[11] Patent Number: 4,763,901
[45] Date of Patent: Aug. 16, 1988

[54] TENNIS ELBOW BRACE

[76] Inventor: Howard S. Richter, 26 Suzanne Rd., Lexington, Mass. 02173

[21] Appl. No.: 818,487

[22] Filed: Jan. 13, 1986

Related U.S. Application Data

[63] Continuation-in-part of Ser. No. 744,928, Jun. 14, 1985, abandoned.

[51] Int. Cl.⁴ ............................................... A63F 5/24
[52] U.S. Cl. ..................................... 273/29 R; 128/77; 128/25 R; 273/DIG. 30
[58] Field of Search .............. 273/26 C, 191 B, 29 A, 273/189 R, 189 A, 54 B, 75, 173 R, DIG. 30; 2/76, 311; 128/77, 87, 88, 80 C, 80 E, 68, 90, 94, 134, DIG. 15, 80 R, 80 G

[56] References Cited

U.S. PATENT DOCUMENTS

| | | | |
|---|---|---|---|
| 1,340,630 | 5/1920 | Maddox | 128/77 |
| 1,402,282 | 1/1922 | Chevries | 128/80 E |
| 2,578,108 | 12/1951 | Thornton | 128/80 F |
| 3,527,208 | 9/1970 | Baker | 128/80 E |
| 3,785,371 | 1/1974 | Lewis | 128/77 |
| 3,859,991 | 1/1975 | Theodores | 128/80 E |
| 3,976,057 | 8/1976 | Barclay | 124/130 |
| 4,299,214 | 11/1981 | Sweitzer | 128/165 |
| 4,436,088 | 3/1984 | Finnieston | 128/77 |

*Primary Examiner*—Richard C. Pinkham
*Assistant Examiner*—T. Brown
*Attorney, Agent, or Firm*—Hamilton, Brook, Smith & Reynolds

[57] ABSTRACT

A surgico-athletic device to be worn by an athlete for preventing or reducing inflammation, further injury and the discomfort of tennis elbow including upper and lower inelastic armbands (2, 4) which encircle the arm above and below the elbow is disclosed. There is an element (6) in the form of an inelastic strap connecting the armbands to control the distance between them and to limit the arm from being fully extended. The armbands are made of inelastic padded woven fabric and are of a length sufficient to encircle the arm. Hook and pile securing material (20, 22) permits the armbands to be adjustably tightened around the arm above the biceps and below the elbow. Liners (60) may be provided to prevent skin from being pinched or squeezed by fastening loops (28).

10 Claims, 4 Drawing Sheets

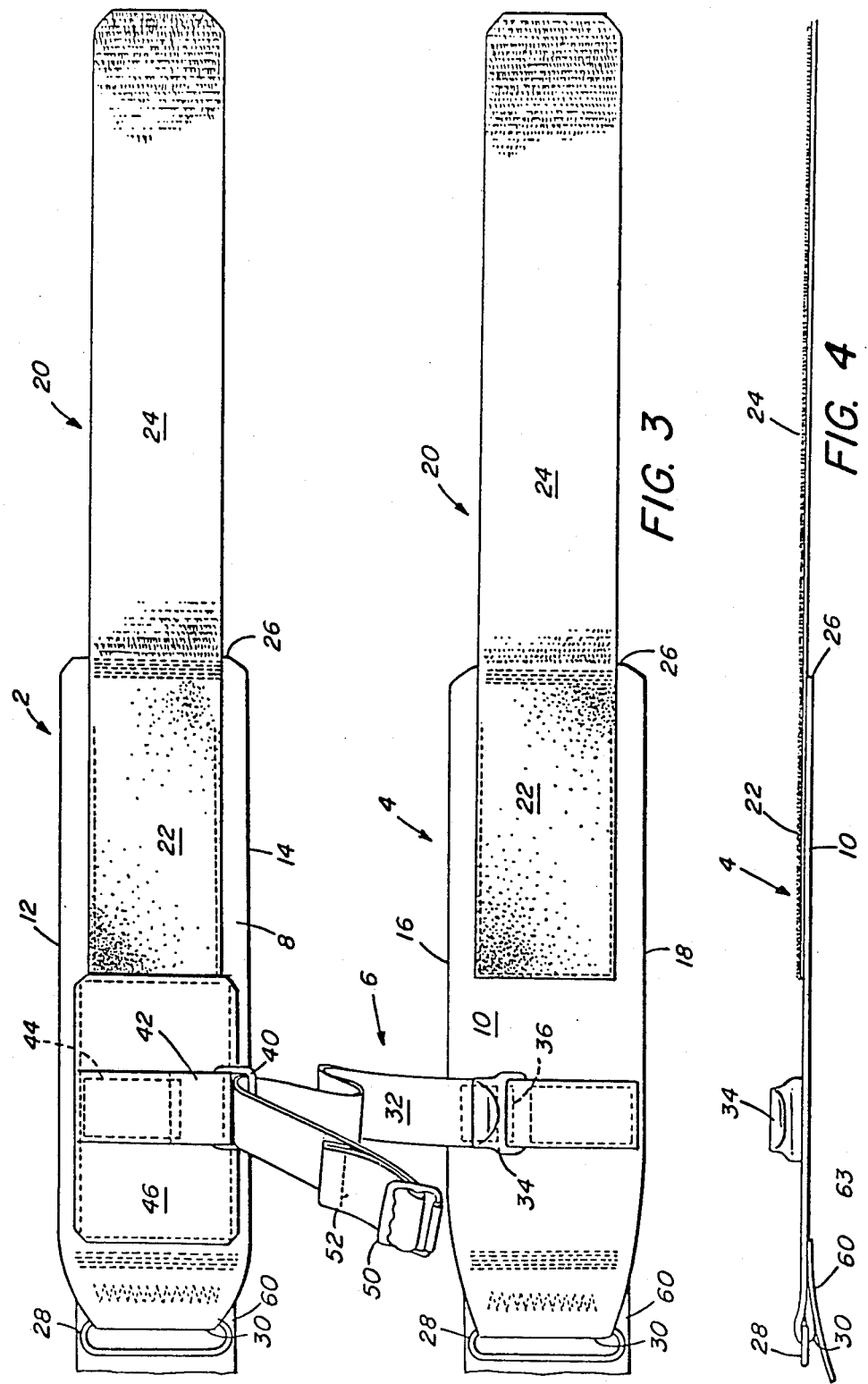

TENNIS ELBOW BRACE

RELATED APPLICATION

This application is a Continuation-in-Part of my co-pending application Ser. No. 744,928 filed June 14, 1985, for "Tennis Elbow Brace".

DESCRIPTION

1. Field of the Invention

This invention pertains to surgico-athletic devices and more particularly is embodied in an arm brace which can be used to prevent or reduce the discomfort resulting from the condition commonly known as "tennis elbow".

2. Background of the Invention

The common term "tennis elbow" refers to a painful arm or elbow condition most often experienced by tennis players but also by racketball players, platform tennis players, people who throw baseballs, softballs, or footballs, javelin throwers, and others.

Although the cause of this disorder is not completely understood, it is likely that repeated impacts of a ball upon the racket are transmitted to the arm of a player, thereby causing the trauma. The offending motions are probable twisting of the forearm and sudden extension of the elbow joint into a fully extended and locked position.

The major symptom of tennis elbow is pain which is aggravated by the above-mentioned motions. The pain is probably caused by inflammation of the ligaments that connect the two bones of the forearm, the radius and ulna, and by inflammation of the tendons of the muscles of the forearm at the points where those tendons attach to the upper arm or humerus. These tendons are attached to the humerus at the spurs, called epicondyles, at the elbow end of the humerus.

Tenderness to pressure upon one of the epicondyles is usual. In the absence of such tenderness, the diagnosis of tennis elbow or "epicondylitis" is doubtful. Tenderness of the medial epicondyle, the spur nearer the torso, is common in players who suddenly extend the elbow during a strong or powerful serve. Tenderness of the lateral epicondyle, the spur facing away from the body, is common in intermediate players who extend the elbow forcefully at the end of the backhand ground stroke.

In addition to rest or exercise to strengthen the arm muscles, tennis elbow is most frequently treated with anti-inflammatory drugs such as aspirin, Indocin and other non-steroidal anti-inflammatory agents, Prednisone, injections of cortisone and, as a last resort, surgery. Preferable to treatment by drugs or surgery would be a natural, non-medication, non-injection, non-surgical treatment not only for preventing the condition but also for reducing the discomfort of the condition after it has occurred.

Applicant has determined that the effects of tennis elbow are markedly diminished or prevented by two procedures. The first is the application of pressure to those portions of the player's arm directly below the medial and lateral epicondyles. Such a procedure apparently prevents or reduces the pulling and twisting action of the tendon connections onto the epicondyles in such a manner that trauma is reduced. The second procedure is the restriction of extreme extension of the elbow joint so that direct trauma to the joint is avoided.

U.S. Pat. No. 3,970,081 to Applegate discloses a brace which is worn on the forearm near the elbow and which reduces the pain in the joint associated with tennis elbow. The brace includes a sleeve of stretchable fabric secured by a strap as it encircles the arm and a pad for applying pressure directly to the traumatized area. While the Applegate support is intended to reduce pain, it does not restrict the elbow from straightening into a fully extended and locked position.

U.S. Pat. No. 3,785,371 to Lewis, in an attempt to prevent the elbow from fully straightening or locking, discloses an arm brace which is an elastic sleeve including a pair of hinges secured to opposite sides of the sleeve. The hinges are secured by crisscrossed straps in the form of a Figure 8. Unfortunately, the elbow can extend fully and fairly easily inside the brace, thus decreasing its effectiveness.

U.S. Pat. No. 4,191,373 to Lancellotti discloses an even more complicated and heavier brace which, while possibly being capable of preventing the full extension of the arm because of its complexcity and weight, reduces the player's maneuverability and speed.

It is accordingly an object of this invention to produce a surgico-athletic device intended to be worn by an athlete playing a racket sport not only to prevent the condition known as tennis elbow but also to reduce discomfort, further injury and inflammation caused thereby, while allowing the player to continue to play. The device should be lightweight in order to permit the player reasonable freedom and flexibility of the arm, yet prevent full extension at the elbow; the device should simultaneously apply pressure below the elbow joint to restrict damaging rotatory tendon motion.

SUMMARY OF THE INVENTION

The invention is embodied in a surgico-athletic brace worn by an athlete. It includes upper and lower soft inelastic armbands intended for encircling the arm above and below the elbow. Means are provided for connecting the bands to each other to limit the distance between them in order to restrict the elbow from being extended fully. Each of the bands comprises a strip of inelastic, padded, woven fabric of a length sufficient to encircle the arm. A strip of contiguous hook and pile securing material is joined to the exterior surface of each band; the pile portion of the securing material overlays each band and the hook portion extends from one end of each band. A fastening loop is secured to the end of each band opposite the hook and pile material so that the hook portion of the securing material can be threaded through in order to reverse its direction so that it can be attached to the pile portion of the securing material.

The means for connecting the two bands is a narrow, inelastic strap which is secured to the lower encircling band substantially at right angles to its marginal edges. A loop is secured to the lower margin of the upper encircling band so that the connecting strap can be threaded through and returned to the lower encircling band, where it is attached by an adjustable latching device. The effective length of the connecting strap can be adjusted by this latching device.

An additional feature of the invention includes a sheet of flexible liner located in contact with a portion of the interior surface of each encircling band to prevent skin from being squeezed or pinched when the bands are being tightened on the arm. One end of the liner is secured to the band adjacent to the fastening loop; its remaining edges are free. This will permit a relative sliding motion to take place between the liner and the band. The arm engaging surface of the liner may, if desired, be "flocked" to produce frictional engagement with the skin, while the band engaging surface of the liner is smooth to facilitate the relative sliding motion with the band.

The above details and unique features of the invention, including various novel details of the construction and combinations of its parts, will now be described in more detail with reference to the accompanying drawings and pointed out in the claims. The particular surgico-athletic brace embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 3 is a top plan view of the brace, and

FIG. 4 is a side elevation of the lower arm encircling band and

PREFERRED EMBODIMENT OF THE INVENTION

The description that follows, including the drawings, describes and illustrates the invention with reference to a right handed wearer; "upper" and "lower" would simply be reversed for a left handed player.

Figure 1:
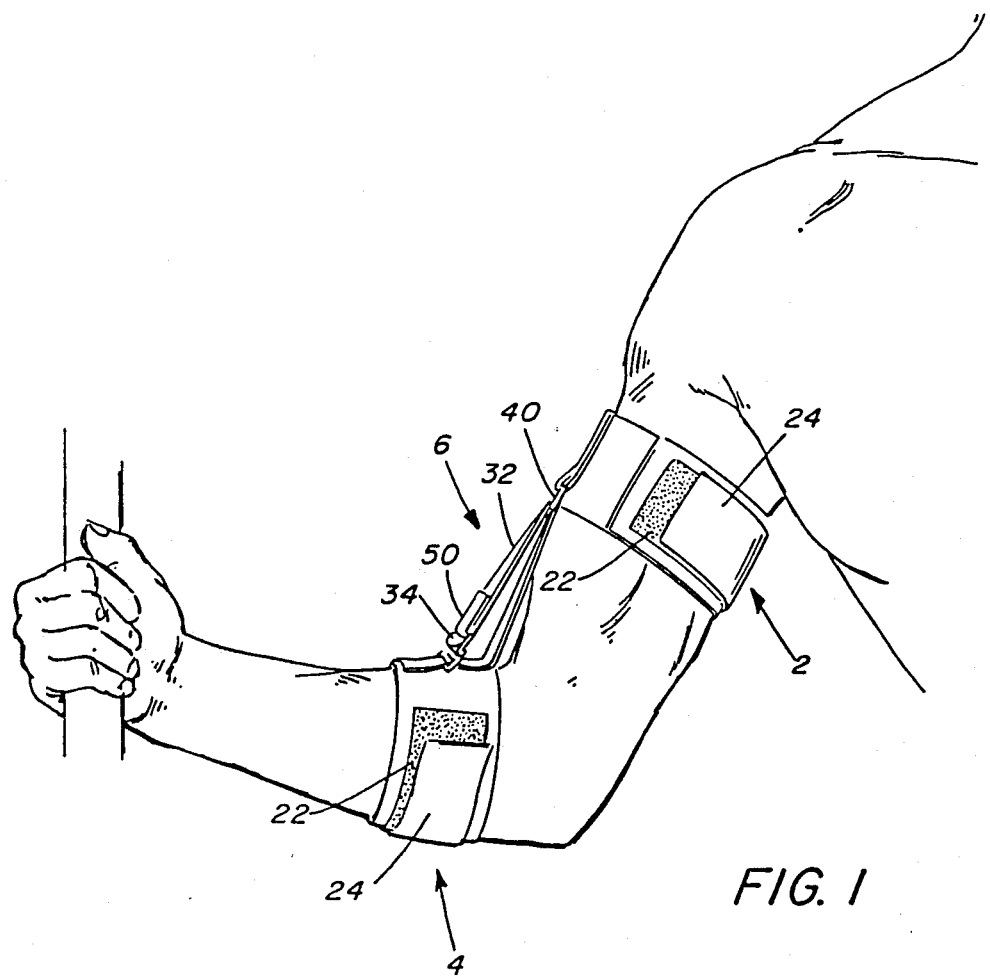
FIG. 1 is a perspective view of an athlete wearing a "tennis elbow" brace made in accordance with features of the present invention.

A surgico-athletic brace embodying features of the invention includes an upper and lower inelastic armband 2 and 4 respectively. The upper band encircles the arm above the biceps muscle and the lower band encircles the forearm just below the elbow as seen in FIG. 1. Connecting means 6 is employed to connect the encircling bands, thereby controlling the distance between them and limiting the elbow from being fully extended.

The bands 2 and 4 comprise a strip 8 and 10, respectively, of inelastic, padded, woven fabric having a length sufficient to encircle the arm. A foam elastomer, such as rubber, has been found satisfactory as padding. Woven cotton or blends of cotton and polyesters possessing high tensile strength have been found satisfactory for the upper surfaces of the bands. For the arm-engaging or inner surface of the bands, where it is desired to have good frictional engagement with the skin so that arm motion cannot cause the armbands to slide toward each other and allow the elbow to extend completely, knitted fabrics of cotton or blends of cotton and polyesters have proven satisfactory.

The upper band 2 has an upper marginal edge 12 and lower marginal edge 14. Similarly, the lower band 4 has an upper marginal edge 16 and lower marginal edge 18. Each band has a strip 20 of contiguous hook and pile securing material of the type sold under the trademark VELCRO. The hook and pile material is joined to the exterior surface of each band, with the pile portion 22 overlaying the band, and the hook portion 24 extending from one end 26 of the band.

Figure 2:
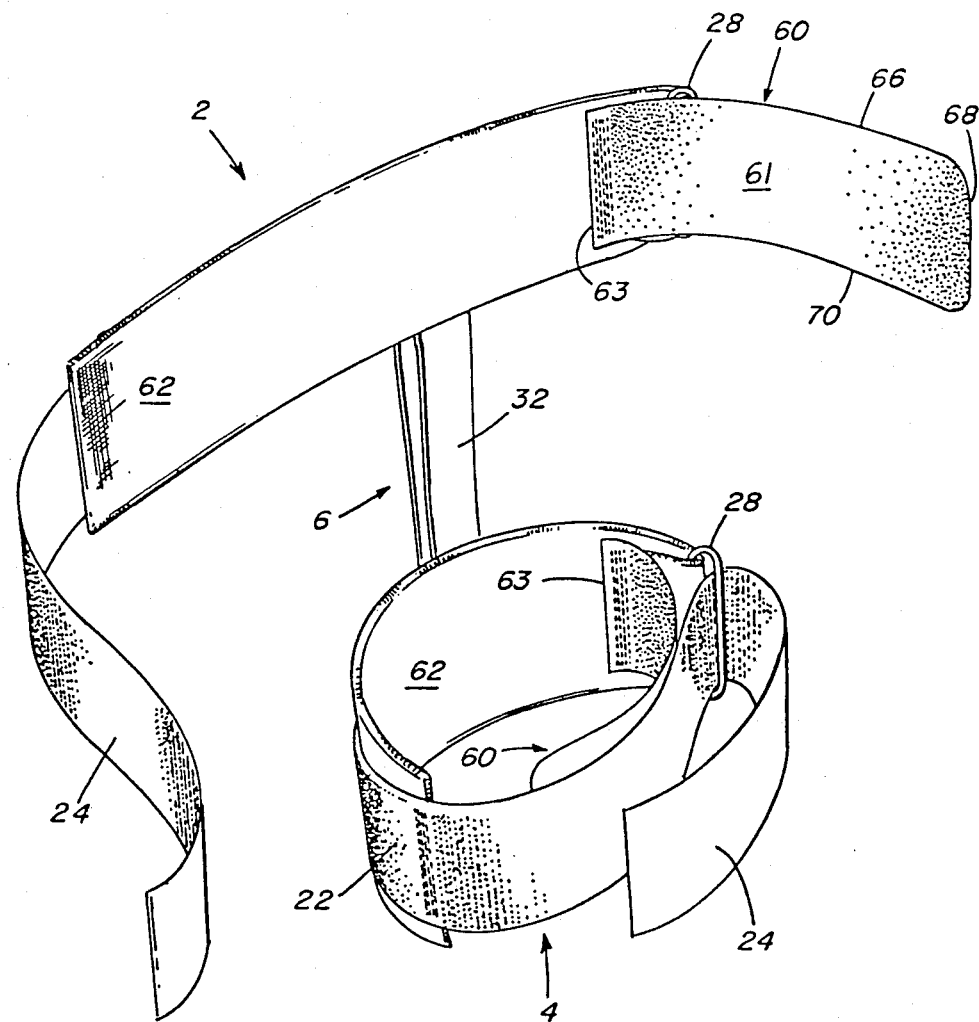
FIG. 2 is a perspective view of the brace exposing its inner or arm engaging surfaces.

A metallic fastening loop 28 is secured to the opposite end 30 of each band; through this loop the hook portion 24 of the securing material is threaded to reverse direction as shown in FIG. 2 to become adjustably engageable with the pile portion 22.

After being placed around the arm as shown in FIG. 1, each armband is tightened by drawing the hook portion of the securing material through the loop 28 and placing it in engagement with the pile portion. The position of the lower armband, as seen in FIG. 1, is such as to apply pressure to reduce the discomfort of tennis elbow if the condition already exists. The facts that the bands are inelastic and padded cause them to remain in position, not only providing the desired comfort but also preventing the elbow from being snapped into a fully extended and locked position.

The connecting means 6 includes an inelastic flexible strap 32 which is secured to the lower band 10 substantially perpendicular to its marginal edge 16. A latch 34 is secured to the strap at the lower band by a strip of stiff material such as leather secured to the band by stitching 36, or its equivalent. A metallic fastening loop 40 is secured to the upper band 2 approximately at its lower marginal edge 14. It is held securely in place by a strip of stiff material such as leather 42 folded under and secured by stitching 44, to an underlying pad 46 also of stiff inelastic material such as leather or the like. The pad 46 is also secured by stitching or the equivalent to the upper band 2. The pad 46 prevents pulling of the armband 2 away from the arm, thus enhancing the inelasticity necessary for preventing complete elbow extension. Mating latching means in the form of a buckle 50 is adjustably positioned on the strap 32 between its ends. Since the buckle 50 is adjustable along the strap 32, the distance between the bands is adjustable by pulling on the free end 52 of the strap 32 after the bands have been placed around the arm, as seen in FIG. 1. The free end 52 of the strap is sewn under, to prevent loss of buckle 50.

Referring to FIG. 1, the upper band 2 is placed around the upper arm just above the biceps muscle and is tightened by pulling the hook portion 24 of the fastening material engaging it with the pile material 22. Similarly, the lower band is placed around the arm just below the elbow and tightened by the hook and pile material. The buckle 50 on the connecting strap 32 is engaged with the clasp 34 and the strap tightened just enough to prevent the elbow from being fully extended.

As an additional feature, to prevent skin from being pinched and squeezed into the loops 28 when the bands 2 and 4 are tightened on the arm, a strip of flexible plastic liner material 60 (FIG. 2) is attached to the interior surface 62 of each band. One edge 63 of the liner is secured to the underside of the band near the fastening loop 28 and the remaining edges 66, 68 and 70 are free. As a result, relative sliding motion between the liner and the band can take place when each band is being positioned around the arm. The arm-engaging surface 61 may, if desired, be "flocked" to produce good frictional engagement with the skin but the opposite or band-engaging surface of the liner is smooth to permit the sliding motion between it and the band.

Figure 5:
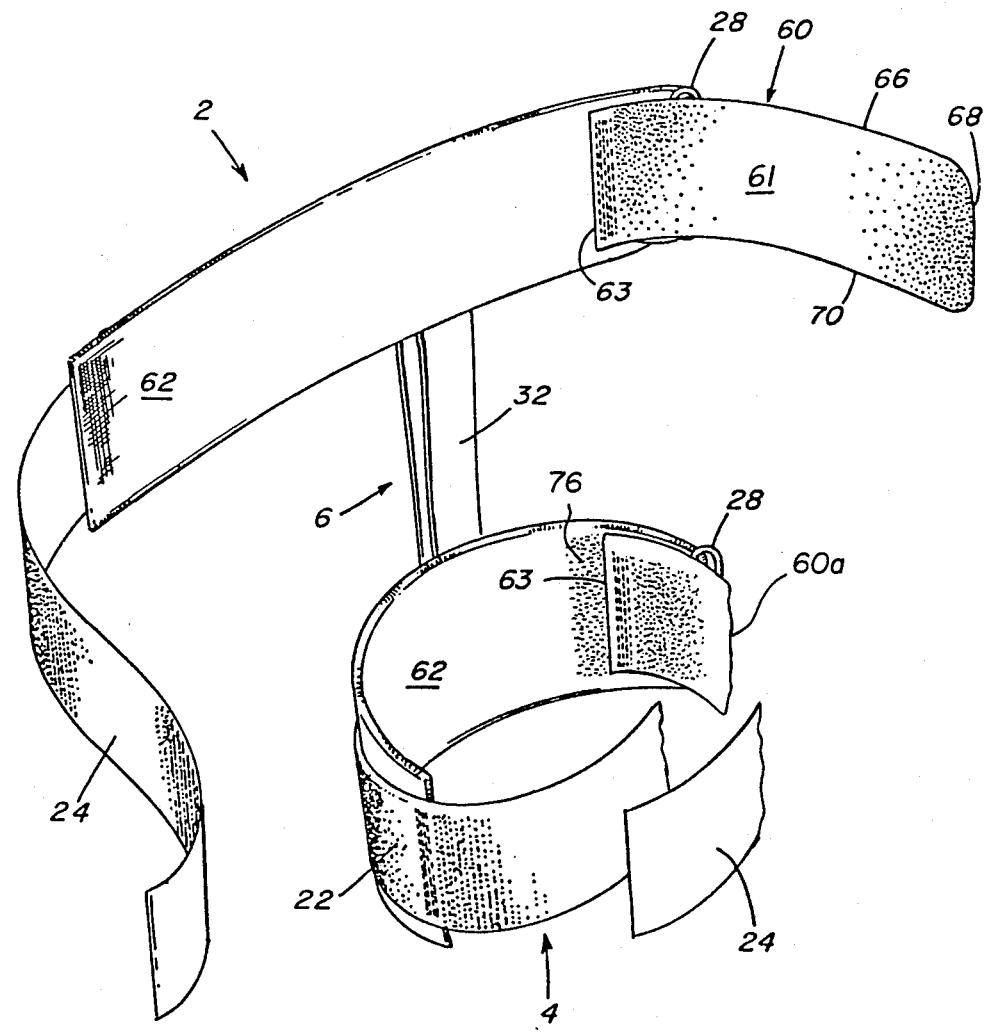
FIG. 5 is a view similar to FIG. 2 showing an alternative construction of the flexible liner.

Referring to FIG. 5, there will be seen an alternative construction to the flexible plastic liner 60 of the FIG. 2 embodiment. The strip of flexible plastic liner 60A is shorter than the liner 60 of the FIG. 2 embodiment but is long enough to cover the loop 28 when the bands 2 and 4 are tightened on the arm.

Whereas the liner 60A may be attached to the respective bands 2 or 4 by stitching adjacent the edge 63 as in the FIG. 2 embodiment, in the FIG. 5 embodiment it is removable for the purpose of replacement or cleaning. The inner surface of the liner 60A and the facing surface of the arm encircling band are provided with hook and pile material 76. Not only is the liner removable but it is repositionable relative to the loop 28 to suit the comfort of the wearer.

Thus, it will be seen that a surgico-athletic brace made in accordance with this invention not only prevents the arm from being fully extended in a tennis or other athletic stroke but produces therapeutic pressure to protect a traumatized area.

Labeling the "lower" band 10 and the "upper" band 12 as such applies only to right-hand players. Left-handed players need merely reverse the two and the device is applied as easily, and is equally effective.

I claim:

1. A surgico-athletic device to be worn by an athlete for preventing or reducing inflammation, further injury and the discomfort of tennis elbow comprising:
   a. an upper and a lower inelastic armband of a length sufficient to encircle the arm above and below the elbow respectively, the encircling armbands each comprising a strip of inelastic, padded, woven fabric and each having an upper and a lower marginal edge;
   b. means connecting the encircling armbands to adjustably control the distance between them to limit the arm from being fully extended;
   c. a strip of contiguous hook and pile securing material joined to the exterior surface of each armband, the pile portion overlaying a portion of the armband and the hook portion extending from one end of the armband;
   d. a fastening loop, secured to the end of the armband opposite to the end from which the securing material extends, through which loop the hook portion of the securing material is threaded to reverse direction and become adjustably engageable with the pile portion;
   e. the connecting means comprising an inelastic strap secured to the lower armband transversely of and extending from the upper marginal edge, a loop secured to the upper armband proximate its lower marginal edge through which loop the strap is threaded to reverse direction, latching means secured to the inelastic strap at the lower armband and mating latching means adjustably positioned on the strap between its ends to adjust the effective length of the strap to control the distance between the armbands when the latching means are engaged.

2. Surgico-athletic device according to claim 1, wherein a sheet of flexible plastic liner material is located adjacent to the fastening loop of each armband, one transverse marginal edge of the liner being secured to the inner surface of the armband and extending beyond the fastening loop and the remaining edges of the plastic liner being free.

3. Surgico-athletic device according to claim 1, wherein a sheet of flexible plastic liner material is located adjacent to the fastening loop of each armband, one transverse marginal edge of the liner being secured to the inner surface of the armband and extending beyond the fastening loop and the remaining edges of the plastic liner being free, and wherein the arm engaging surface of the liner is flocked to improve frictional engagement with the skin.

4. Surgico-athletic device according to claim 1, wherein a sheet of flexible plastic liner material is located adjacent the fastening loop of each armband, one transverse marginal edge of the liner being secured to the inner surface of the armband and extending beyond the loop and the remaining edges of the plastic liner being free, and wherein the armband engaging surface of the liner is smooth to permit relative sliding motion between the liner and the armband.

5. Surgico-athletic device according to claim 1, wherein the upper armband includes a stiffening pad of inelastic material in the area where the fastening loop is secured to prevent arm motions from pulling the armband away from the arm.

6. Surgico-athletic device according to claim 1, wherein the encircling armbands are lined on their interior arm engaging surfaces to produce comfort and to improve frictional engagement with the skin, so that arm motion cannot cause the armbands to slide toward each other, thus allowing the elbow to extend completely.

7. A surgico-athletic device to be worn by an athlete for preventing or reducing inflammation, further injury and the discomfort of tennis elbow comprising:
   a. an upper and a lower inelastic armband of a length sufficient to encircle the arm above and below the elbow respectively, the encircling armbands each comprising a strip of inelastic, padded, woven fabric and each having an upper and a lower marginal edge;
   b. means connecting the encircling armbands to adjustably control the distance between them to limit the arm from being fully extended;
   c. a strip of contiguous hook and pile securing material joined to the exterior surface of each armband, the pile portion overlaying a portion of the armband and the hook portion extending from one end of the armband;
   d. a fastening loop, secured to the end of the armband opposite to the end from which the securing material extends, through which loop the hook portion of the securing material is threaded to reverse direction and become adjustably engageable with the pile portion;
   e. the connecting means comprising an inelastic strap secured to the lower armband transversely of and extending from the upper marginal edge, a loop secured to the upper armband proximate its lower marginal edge through which loop the strap is threaded to reverse direction, latching means secured to the inelastic strap at the lower armband and mating latching means adjustably positioned on the strap between its ends to adjust the effective length of the strap to control the distance between the armbands when the latching means are engaged, and
   f. a sheet of flexible plastic liner material located adjacent to the fastening loop of each armband, one transverse marginal edge of the liner being secured to the inner surface of the armband and extending beyond the fastening lop and the remaining edges of the plastic liner being free.

8. Surgico-athletic device according to claim 7, wherein the arm engaging surface of the liner is flocked to improve frictional engagement with the skin.

9. Surgico-athletic device according to claim 7, wherein the upper armband includes a stiffening pad of inelastic material in the area where the fastening loop is secured to prevent arm motions from pulling the armband away from the arm.

10. Surgico-athletic device according to claim 7, wherein the arm engaging surface of the liner is flocked to improve comfort and increase frictional engagement with the skin.

* * * * *